United States Patent
Shekunov et al.

(10) Patent No.: US 7,767,118 B2
(45) Date of Patent: *Aug. 3, 2010

(54) NANOPARTICLES FROM SUPERCRITICAL FLUID ANTISOLVENT PROCESS USING PARTICLE GROWTH AND AGGLOMERATION RETARDANTS

(75) Inventors: Boris Y. Shekunov, Aurora, OH (US); Pratibhash Chattopadhyay, North Royalton, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 51 days.

This patent is subject to a terminal disclaimer.

(21) Appl. No.: 10/531,160

(22) PCT Filed: May 28, 2004

(86) PCT No.: PCT/US2004/017211

§ 371 (c)(1),
(2), (4) Date: Apr. 12, 2005

(87) PCT Pub. No.: WO2004/108265

PCT Pub. Date: Dec. 16, 2004

(65) Prior Publication Data
US 2006/0039983 A1   Feb. 23, 2006

Related U.S. Application Data

(60) Provisional application No. 60/475,547, filed on Jun. 3, 2003.

(51) Int. Cl.
*A61K 9/14* (2006.01)
*B29B 9/00* (2006.01)

(52) U.S. Cl. .................. 264/14; 424/400; 424/489; 424/497

(58) Field of Classification Search .................. 424/489
See application file for complete search history.

(56) References Cited

U.S. PATENT DOCUMENTS

| 5,043,280 | A |  | 8/1991 | Fischer et al. |
| 5,389,263 | A |  | 2/1995 | Gallagher et al. |
| 5,707,634 | A |  | 1/1998 | Schmitt |
| 5,770,559 | A |  | 6/1998 | Manning et al. |
| 5,874,029 | A | * | 2/1999 | Subramaniam et al. ....... 264/12 |
| 6,576,264 | B1 |  | 6/2003 | Henriksen et al. |
| 6,620,351 | B2 |  | 9/2003 | Gupta et al. |
| 6,974,593 | B2 | * | 12/2005 | Henriksen et al. ........... 424/490 |
| 2003/0064029 | A1 | * | 4/2003 | Tarara et al. .................. 424/45 |

FOREIGN PATENT DOCUMENTS

| EP | 0542314 A1 | 5/1993 |
| WO | WO 95/01221 | 1/1995 |
| WO | WO 96/00610 | 1/1996 |
| WO | WO 99/59710 | 11/1999 |

OTHER PUBLICATIONS

Chattopadhyay, P. and Gupta, R., Production of Antibiotic Nanoparticles Using Supercritical CO2 as Antisolvent with Enhanced Mass Transfer, Ind. Eng. Chem. Res., 2001, vol. 40, pp. 3530-3539.
Chattopadhyay, P. and Gupta, R., Protein Nanoparticles Formation by Supercritical Antisolvent with Enhanced Mass Transfer, AIChE Journal, Feb. 2002, vol. 48, No. 2, pp. 235-244.

* cited by examiner

*Primary Examiner*—Michael G Hartley
*Assistant Examiner*—Nabila G Ebrahim
(74) *Attorney, Agent, or Firm*—Rankin, Hill & Clark LLP

(57) ABSTRACT

The present invention provides a method of forming particles using supercritical fluid (SCF). In accordance with the method, one or more growth retardant compounds having both SCF-philic and SCF-phobic groups are present when one or more solute materials reach a supersaturation point and begin to form particle nuclei. The growth retardant compounds can reduce the particle growth rate, increase the nucleation rate and also prevent particle agglomeration. Preferred growth retardant compounds include sugar acetates and fluorocarbons.

7 Claims, 5 Drawing Sheets

NANOPARTICLES FROM SUPERCRITICAL FLUID ANTISOLVENT PROCESS USING PARTICLE GROWTH AND AGGLOMERATION RETARDANTS

BACKGROUND OF THE INVENTION

1. Field of Invention

The present invention relates to methods of forming solid particles using supercritical fluids. More particularly, the present invention relates to methods of forming solid nanoparticles using supercritical fluids and particle growth and agglomeration retardants.

2. Description of Related Art

Supercritical fluids (SCF) are gases or liquids that are compressed above their critical pressure and heated above their critical temperature. The most commonly employed SCF is carbon dioxide ($CO_2$) because of its low cost, non-toxicity and ease of availability. The critical temperature of $CO_2$ is 304.2K and the critical pressure of $CO_2$ is 7.38 MPa.

Several properties make SCF ideal for the production of particles. For example, commonly used organic solvents have large volumetric expansion coefficients and large diffusion coefficients in SCF. SCF exhibits a relatively low viscosity when compared to sub-critical liquids. And, SCF can provide economical operation costs and environmentally benign processing.

In recent years, supercritical fluids such as $CO_2$ have been successfully used to precipitate particles for various drug delivery systems. The two most commonly used SCF based particle-processing techniques include the Rapid Expansion of Supercritical fluid Solution (RESS) process and the Supercritical fluids Anti-Solvent (SAS) process.

The RESS process involves the expansion of a solution comprising a material (e.g., a drug or a drug/polymer mixture) dissolved in SCF through a fine nozzle into a low-pressure chamber causing high supersaturation, nucleation and precipitation of the material dissolved in the SCF in the form of fine particles. Unfortunately the application of this process is limited due to the low polarizability and non-existent dipole moment of $CO_2$, which makes it a poor solvent for most pharmaceuticals and biopolymers. Another major disadvantage of the RESS process is that the fine particles produced upon expansion of the SCF solution tend to exhibit a high degree of agglomeration. In some cases, long chains of connected particles are formed, which render the particles unsuitable for various pharmaceutical applications.

The SAS process uses SCF as an antisolvent to produce particles. It takes advantage of the high solubility or miscibility of organic solvents in SCF. In the SAS process, a solution comprising a material (e.g., a drug or a drug/polymer, lipid and/or wax mixture) dissolved in an organic solvent is injected into the SCF using a fine nozzle. The SCF extracts the organic solvent from the solution thereby causing supersaturation and nucleation of the material, which precipitates in the form of fine particles.

Several variations of the SAS process have been developed in order to obtain better control over the size and morphology of the resulting particles. These variations of the SAS process are known in the art as: Precipitation with Compressed Antisolvents (PCA) (see, e.g., Schmitt, U.S. Pat. No. 5,707,634); Aerosol Spray Extraction System (ASES) (see, e.g., Fischer et al., U.S. Pat. No. 5,043,280, Lim et al., EP 0 542 314 and Manning et al., U.S. Pat. No. 5,770,559); and the Solvent Enhanced Dispersion with Supercritical fluid (SEDS) (see, e.g., Hanna et al., WO95/01221, WO96/00610 and WO99/59710). The disclosures of all of the preceding references are hereby incorporated by reference in their entirety.

Although the techniques referenced above provide several advantages over the conventional SAS process, they are also subject to certain limitations. In most cases, the processes mentioned above are unsuitable for producing particles having diameters smaller than about 500 nm and a narrow size distribution. This is primarily due to the fundamental limitations imposed by the nucleation and growth phenomenon that occurs in the SCF antisolvent process, which tends to precipitate the particles of most materials in the micron size range. In other words, supersaturation is not reached rapidly enough in most cases to cause high nucleation rates and precipitation of particles in the nanometer range.

Different techniques have been developed to increase the supersaturation rate through enhanced mixing of the organic solvent, and the SCF. This has usually been achieved using finer diameter nozzles, coaxial nozzles, mixers and ultrasound devices. Although these techniques are effective, they are not universal and are only effective for some materials. Furthermore, these enhanced mixing techniques pose problems for large-scale pharmaceutical manufacture and processing. For example the use of fine nozzles or coaxial nozzles often introduces problems of low yields and nozzle clogging. Mixers and ultrasound in the supercritical fluid phase also causes problems of material degradation due to high shear and foreign material contamination in the final product.

Another disadvantage of the conventional and the modified SAS technique is that the particles obtained usually tend to form agglomerates. In some cases, the particles obtained are in the form of a fine mesh of connected particles. This is often unsuitable in the pharmaceutical industry, especially for the production of particles for respiration where agglomeration of particles drastically deteriorates the aerodynamic properties of the final product.

BRIEF SUMMARY OF THE INVENTION

The present invention provides a method of forming particles using SCF that overcomes the limitations of conventional SCF particle processing techniques. Particles produced in accordance with the present invention undergo minimal agglomeration and thus possess superior properties as compared to particles produced in conventional SCF processing techniques.

The method of the invention employs one or more compounds that are soluble in SCF and act as particle growth and agglomeration inhibitors during precipitation. In all SCF processes, whether SCF is used as a solvent or an antisolvent, particles are formed via supersaturation, which in turn leads to the formation of nuclei. Particles are obtained when the nuclei formed coalesce together to form large stable entities. In the method of the present invention, one or more SCF soluble compounds hereinafter referred to as "growth retardant compounds" are employed to hinder nuclei coalescence, which results in the precipitation of smaller particles. Apart from affecting nuclei coalescence, the growth retardants also hinder inter particle interaction and thus minimize particle agglomeration.

In the preferred embodiment of the invention, $CO_2$ is used as the SCF, and the growth retardant compounds employed include both $CO_2$-philic and $CO_2$-phobic or solute-philic groups. The solubility of the growth retardant compounds in supercritical $CO_2$ is attributed to the presence of the $CO_2$-philic group(s). The interaction between the growth retardant compounds and the nuclei formed during precipitation, which results in a shielding effect, is attributed to the $CO_2$-phobic group(s). Examples of growth retardant compounds suitable for use in accordance with the method of the invention include sugar acetates, fluorocarbons and block copolymers comprised of polymer blocks selected from the group consisting of polypropylene oxide, polyethylene oxide, poly methacrylic acid (PMMA), poly acrylic acid (PAA), poly vinyl acetate (PVA) and polyethylene oxide (PEO).

The growth retardant compounds can be either introduced into the SCF as part of a solution comprising one or more, materials to be precipitated (e.g., a drug or a drug/polymer) dissolved in an organic solvent, or the growth retardant compounds can be dissolved in the SCF before the material to be precipitated is introduced into the SCF. Both in the RESS and SAS methods of particle processing, during the precipitation step the final particle size is determined by the degree of particle growth due to the nuclei growth and coalescence. The growth retardant compounds present in the SCF, or in some cases co-precipitated in the SCF, protect or shield the nuclei formed and thereby prevent the particles from agglomerating into larger particles. Thus, the method of the present invention facilitates the manufacture of particles using equipment used in the conventional SAS and the RESS techniques, but employs one or more growth retardant compounds to allow for the precipitation of particles having smaller sizes with lesser agglomeration.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
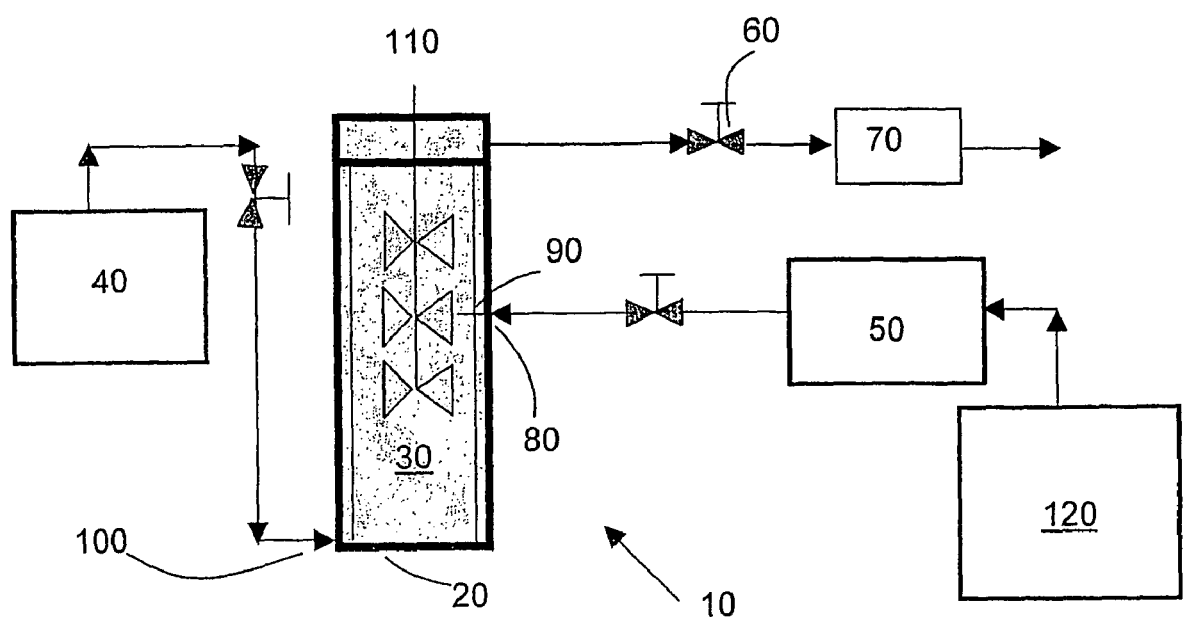
FIG. 1 is a schematic representation of an exemplary apparatus for producing particles in accordance with a first embodiment of the invention.

As previously noted, in the conventional SAS technique, an organic solution containing a known amount of a material to be precipitated (e.g., a drug or a mixture of a drug and a polymer, lipid and/or a wax) is injected into a high-pressure vessel containing SCF. Mass transfer between the organic solvent phase and the supercritical fluid phase causes supersaturation, which leads to the formation of fine nuclei. The nuclei grow due to an influx of solute molecules to the surface to form larger stable particles. The method of the present invention provides control over particle size by affecting both nucleation growth kinetics and by preventing agglomeration, which leads to smaller and more uniform particles.

In one preferred embodiment of the method of the invention, a solution comprising one or more materials to be precipitated into particles dissolved in one or more organic solvents is introduced into a SCF into which has been dissolved one or more growth retardant compounds. As soon as the solution is introduced into the SCF, mass transfer between the organic solvent present in the solution and the SCF phase occurs, which leads to supersaturation and the formation of nuclei comprising the material(s) to be precipitated. The growth retardant compounds present in the SCF surround the nuclei immediately after they are formed and thereby prevent the nuclei from further rapid growth and agglomeration. Hence, particles are precipitated having sizes much smaller than can be obtained using the conventional SAS technique. It will be appreciated that the growth retardant compound(s) can be introduced into the SCF with the solution as opposed to being dissolved in the SCF prior to the introduction of the solution into the SCF.

In another preferred embodiment of the method of the invention, one or more growth retardant compounds are dissolved in the SCF together with one or more materials to be precipitated into particles to form a SCF solution. The SCF solution is then expanded across a pressure drop, preferably through a nozzle into a low-pressure collection chamber. The rapid decompression of the SCF solution causes supersaturation and nucleation leading to particle precipitation. As observed in the SAS process, the size of the resulting particles in the RESS process is also determined by the rate at which supersaturation is reached and by nucleation growth kinetics. In the method of the present invention, during expansion of the SCF the growth retardant compound(s) are also precipitated. The growth retardant compound(s) reduce the nuclei growth rate and coalescence of nuclei into larger agglomerates. Hence, particles are precipitated having sizes much smaller than can be obtained using the conventional RESS technique.

The agglomeration of particles, which is a problem in the conventional SAS and the RESS techniques, is also minimized due to the shielding effect provided by the growth retardant compound(s). In some cases, the particles produced in accordance with the method of the invention exhibit unusual surface properties or crystalline shape changes. This is due to the alteration of nuclei growth rates caused by the presence of the growth retardant compound(s) during precipitation. The growth retardant compound(s) can hinder the growth of one crystalline face thereby creating particles of differing shape and surface characteristics. After the precipitation process is over, the growth retardant compound(s) can easily be removed and separated from the particles because the growth retardant compound(s) are soluble in SCF. The growth retardant compound(s) can conveniently be removed simply by purging the high-pressure precipitation vessel with a SCF such as pure $CO_2$.

Any compounds that comprise both SCF-philic groups, which make the compound soluble in SCF, and SCF-phobic groups, which have an affinity or attraction to the nuclei of the material(s) formed during the precipitation step, can be employed as growth retardant compounds. Examples of growth retardant compounds for use with supercritical carbon dioxide (SC—$CO_2$) include sugar acetates such as sucrose octaacetate and alpha D glucose penta acetate, fluorocarbons such as perfluoro polyethylene(s), and block copolymers comprised of polymer blocks selected from the group consisting of polypropylene oxide, polyethylene oxide, poly methacrylic acid (PMMA), poly acrylic acid (PAA), poly vinyl acetate (PVA) and polyethylene oxide (PEO). When the material(s) to be precipitated into particles is intended for pharmaceutical applications, the growth retardant compounds should be non-toxic.

Particles produced in accordance with the methods of the invention can comprise a single-material or a combination of more than one material. For example, it is possible to produce particles of a drug or a drug that is encapsulated within a coating material or dispersed within a matrix comprising another material such as a polymer, lipid and/or wax. The particles formed in accordance with the methods of the invention tend to be smaller and/or less agglomerated than particles obtained using conventional SCF processing techniques including SAS, RESS, PCA, ASES and SEDS.

A schematic representation of an exemplary apparatus for producing particles in accordance with a first embodiment of the invention is shown in FIG. 1. The apparatus 10 includes a vessel 20, which is preferably tubular and has an inner cylindrical sidewall and first and second ends that are spaced apart from each other to define a cylindrical chamber 30. A supercritical fluid pump 40 and a solution feed pump 50 communicate with the chamber 30. A release valve 60 and a backpressure regulator 70 also communicate with the chamber 30. A thermostat (not shown) controls heating elements 80 that are located proximate to the vessel 20. Disposed within the chamber 30 are a solution inlet nozzle 90, a supercritical fluid inlet 100, and a filter (not shown) to collect the particles.

For the laboratory-scale production of particles, the supercritical fluid pump is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of supercritical fluid. The supercritical fluid pump 40 is in fluid communication with the supercritical fluid inlet 100, and thereby supplies supercritical fluid into the chamber 30.

For the laboratory-scale production of particles, the solution feed pump 50 is preferably a high-pressure liquid chromatography (HPLC) reciprocating pump such as the model PU-2080, which is commercially available from Jasco Inc. (Easton, Md.). Suitable alternative pumps include other reciprocating pumps, diaphragm pumps and syringe type pumps, such as the 1000D or 260D pumps, which are commercially available from Isco Inc. (Lincoln, Nebr.). The solution feed pump 50 is in fluid communication with the solution inlet nozzle 90, and thereby supplies solution into the chamber 30. The solution inlet nozzle 90 is preferably a capillary-type tube, or a tube having non-circular cross-section, for example, a slit, and preferably extends through the sidewall into the chamber 30.

For the laboratory-scale production of particles, the backpressure regulator is preferably a 26-1700 type regulator, which is commercially available from Tescom, USA (Elk River, Minn.) and is interchangeable with other like valves that are known to those of ordinary skill in the art. If desired, a mixer assembly 110 that includes a motor, a shaft extending from the motor and a rotor disposed at a distal end of the shaft, can be located in the chamber 30 in order to ensure adequate mixing.

Preferably, a controller (not shown) communicates with and controls the supercritical fluid pump 40, the solution feed pump 50, the release valve 60, the backpressure regulator 70, the thermostat for the heating elements 80, and the mixer assembly 110. Suitable controllers are well known in the art and are interchangeable therewith.

A solution 120 is pumped by the solution feed pump 50 to the chamber 30. The solution 120 comprises one or more solvents, one or more materials to be precipitated in the form of particles (sometimes hereinafter referred to as "solute(s)"), and one or more growth retardant compounds. The solvent must be at least partially soluble in supercritical fluid. Preferred solvents include alcohols, dimethyl sulfoxide (DMSO), dimethyl formamide (DMF), tetra hydrofuran (THF), acetone, ethyl acetate and methylene chloride.

The material or materials that are to be precipitated into particles (i.e., the solute(s)) can comprise any material that is soluble in the solvent(s). Because the particles produced in accordance with the method of the invention tend to be very small in size and less agglomerated, the material to be precipitated into particles is often a pharmaceutical. Suitable pharmaceutical solute materials include, for example, medicinal agents, biologically active materials, sugars, viral materials, diagnostic aids, nutritional materials, proteins, peptides and animal and/or plant extracts. The material can also comprise one or more non-pharmaceutical solute materials such as, for example, agricultural chemicals, dyes, explosives, paints, polymer precursors, alkyloids, alkaloids, cosmetics, insecticides, pigments, toxins, antigens, enzymes, catalysts, nucleic acids, and combinations thereof.

It will be appreciated that the method of the invention can be utilized to produce particles comprising two or more different solute materials. If multiple soluble materials are dissolved in the solvent, the resultant particles will tend to contain all of the solute constituents. If micro-encapsulates, microspheres, coated particles or co-precipitated particles are desired, a carrier or matrix material can be dissolved in the same solution with a drug or other solute material. Preferred matrix materials include polymers, fillers, disintegrants, binders, solubilizers, excipients, and combinations thereof. In particular, the matrix materials can be, for example, polysaccharides, polyesters, polyethers, polyanhydrides, polyglycolides (PLGA), polylactic acids (PLA), polycaprolactones (PCL), polyethylene glycols (PEG), and polypeptides.

In the presently most preferred embodiment of the invention, the SCF is SC—$CO_2$. Carbon dioxide is supercritical when certain environmental parameters are met, namely, when the carbon dioxide is above about 304.2 Kelvin (K) and above about 7.38 megaPascal (MPa). Suitable alternative supercritical fluids include nitrous oxide, dimethylether, straight chain or branched C1-C6-alkanes, alkenes and combinations thereof. Preferable alkanes and alcohols include ethane, propane, butane, isopropane and the like. The SCF chosen must be compatible with the solute material(s) to be used in the process. It is important that the solute material(s) be generally insoluble in the SCF, whereas the solvent(s) should be generally soluble in the SCF.

The growth retardant compound can be any compound that is soluble in the SCF and possesses both SCF-philic and either SCF-phobic or solute-philic groups. The growth retardant compounds (e.g., sugar acetates containing carbonyl groups) can undergo Lewis acid and Lewis base interactions with the SCF, thereby readily dissolving in them and causing a growth retardant effect upon co-precipitation due to interaction with the solute. Preferred growth retardant compounds include, for example, sugar acetates, fluorocarbons and block copolymers comprised of polymer blocks selected from the group consisting of polypropylene oxide, polyethylene oxide, poly methacrylic acid (PMMA), poly acrylic acid (PAA), poly vinyl acetate (PVA) and polyethylene oxide (PEO).

The first embodiment of the method of the invention will be described with reference to FIG. 1. The apparatus 10 is first assembled. The supercritical fluid pump 40 is used to supply supercritical fluid into the chamber 30 up to a predetermined pressure at a constant flow rate. The pressure inside the vessel 20 is maintained constant using the backpressure regulator 70. A thermostat that controls the heating elements 80 is used to maintain the temperature of the vessel 20 at a predetermined temperature. Once the vessel 20 is pressurized with SCF at the desired operating temperature, pressure and flow rate, the solution feed pump 50 is used to supply the solution 120 comprising a solvent, a solute material to be precipitated and the growth retardant compound through the solution inlet nozzle 90 and into the chamber 30.

If a mixing assembly 110 is employed within the chamber 20, the mixing assembly 110 is engaged so that the motor rotates the rotor prior to the introduction of the solution 120 into the SCF-filled chamber 20. The spinning rotor is employed to intimately mix SCF with the solution during the precipitation process.

As soon as the liquid solution is introduced into the vessel, mass transfer of the solvent present in the solution into the SCF results in supersaturation and nucleation of the solute material. The growth retardant compound present in the solution also immediately dissolves in the supercritical fluid phase. In convention processes, the nuclei of solute material obtained in the vessel now undergo growth and coalescence and thus form larger stable particles. In the method of the present invention, however, the growth retardant compound present in the SCF reduces the growth rate of the nuclei and thereby increases the solution supersaturation and minimizes the opportunities the nuclei have to coalesce and form agglomerates. The particles precipitated in the chamber 30 can be collected from the bottom of the chamber. A mixture comprising the SCF, the solvent(s) and the growth retardant compound(s) is removed from the chamber through the backpressure regulator 70 and the filter. The filter separates the particles present in the vessel from the SCF stream.

After the particles have been precipitated, the particles are typically subjected to a cleaning step whereby any residual solvent and/or growth retardant compound present inside the chamber is removed. The flow of solution 120 into the vessel 20 is stopped. However, the flow of SCF through the vessel 20 is maintained for a time sufficient to purge the residual solvent and the growth retardant compound present in the supercritical fluid phase inside the vessel. After cleaning, the vessel is depressurized to obtain the particles.

The resultant particles can include crystalline, semi-crystalline and amorphous powders of small-molecules, powders of polymeric and biological molecules, specifically but not limited to biologically-active medicinal substances, therapeutic proteins and peptides intended for different drug delivery applications. The particles can be in the form of spheres or capsules, and can include, for example, a combination of therapeutic or biologically active agents coated or incorporated into a carrier polymer or excipient. The spheres and capsules are generally suitable for controlled, sustained or modified drug release, taste masking or modifying, and drug solubilization. Particles produced in accordance with the methods of the invention preferably have an average particle size of less than 10 micron and more than 300 nm.

Figure 2:
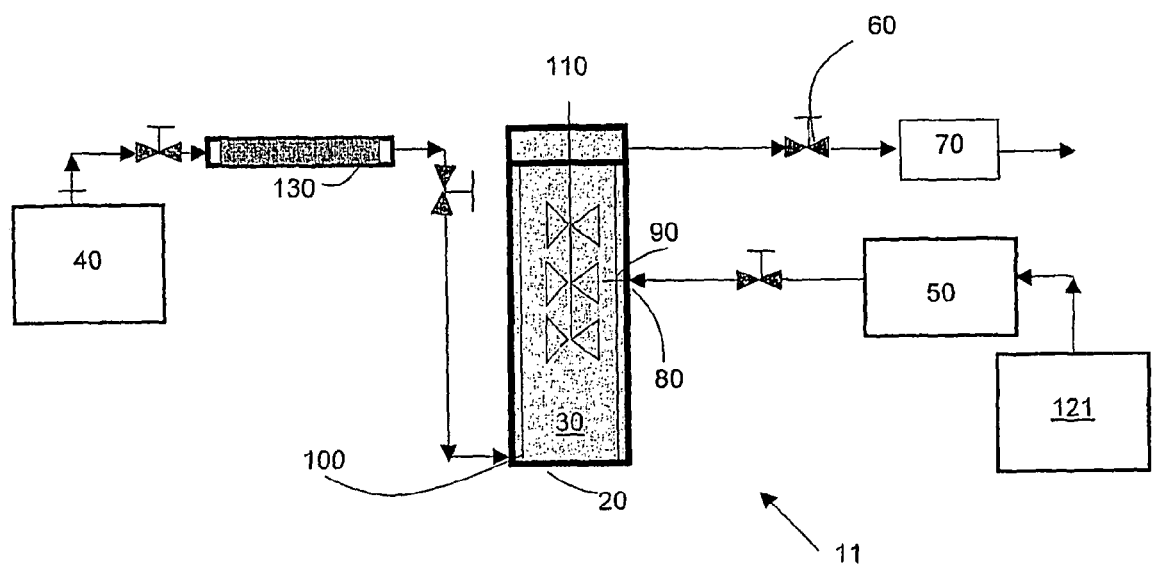
FIG. 2 is a schematic representation of an exemplary apparatus for producing particles in accordance with a second embodiment of the invention.

A schematic representation of an exemplary apparatus 11 for producing particles in accordance with a second embodiment of the invention is shown in FIG. 2. Because the apparatus 11 shown in FIG. 2 is similar, in many respects, to the apparatus 10 shown in FIG. 1, the same reference numbers used in FIG. 1 are also used to identify identical components of the apparatus 11 shown in FIG. 2. The primary difference between the apparatus 10 shown in FIG. 1 and the apparatus 11 shown in FIG. 2 is the addition of a high-pressure extraction column 130 between the SCF pump 40 and the SCF inlet 100.

In accordance with the second embodiment of the invention, a thermostat controls heaters that are used to maintain the temperature of the extraction column 130 at a predetermined constant temperature. The extraction column 130 is packed with one or more suitable growth retardant compounds. SCF from the SCF pump 40 flows through the extraction column 130 and becomes saturated with the growth retardant compound(s) prior to entering the chamber 30. Thus unlike the first embodiment of the invention where the growth retardant compound was introduced with the solution 120 through the solution inlet nozzle 90, in the second embodiment of the invention the growth retardant compound is pre-dissolved in the SCF prior to the introduction of the SCF in the chamber 30.

Although the growth retardant compound is introduced in a different manner, particle precipitation occurs in the second embodiment of the invention in essentially the same manner as in the first embodiment. A solution 121, which comprises one or more solvents and one or more solute materials to be precipitated, is introduced into the chamber 30 containing the SCF and the pre-dissolved growth retardant compound. Mass transfer of the solvent(s) present in the solution into the SCF results in supersaturation and nucleation of the solute material(s). As in the first embodiment of the invention, the growth retardant compound shields the nuclei of solute material(s) by surrounding the surfaces thereof, which limits or minimizes the opportunity for the nuclei to coalesce and form large particles. The growth retardant compound also prevents inter particle interaction once precipitation is complete, and thus aids in preventing particle agglomeration.

The particles can be collected from the bottom of the vessel 20. The mixture of SCF, solvent and growth retardant compound is removed from the chamber through the backpressure regulator 70 and a filter (not shown). Use of a filter helps separate any particles that may be present in SCF stream.

Once the precipitation process is complete the flow of solution 121 into the vessel 20 is stopped. Pure SCF is introduced into the precipitation vessel 20 by bypassing the extraction column 130 containing the growth retardant compound (s) using valves. The flow of pure SCF through the vessel 20 is maintained for a time sufficient to completely purge any residual solvent and the growth retardant compound present in the supercritical fluid phase inside the vessel. After cleaning, the vessel is depressurized to obtain the particles of the solute material(s).

Figure 3:
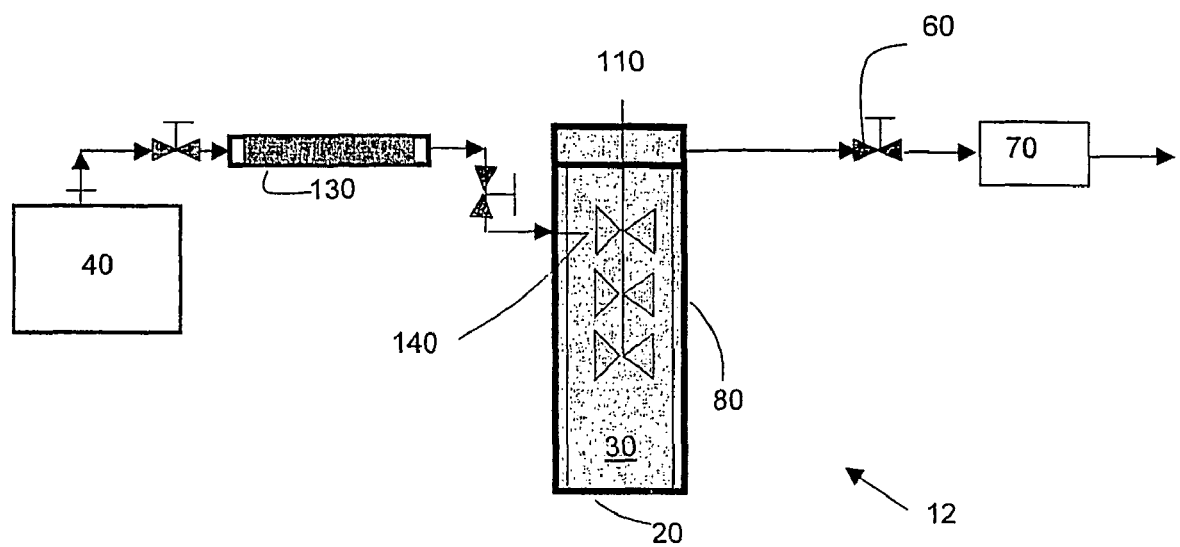
FIG. 3 is a schematic representation of an exemplary apparatus for producing particles in accordance with a third embodiment of the invention.

A schematic representation of an exemplary apparatus 12 for producing particles in accordance with a third embodiment of the invention is shown in FIG. 3. Because the apparatus 12 shown in FIG. 3 is similar, in many respects, to the apparatuses 10, 11 shown in FIGS. 1 and 2, the same reference numbers used in FIGS. 1 and 2 are also used to identify identical components of the apparatus 12 shown in FIG. 3. The primary difference between the apparatus 11 shown in FIG. 2 and the apparatus 12 shown in FIG. 3 is that there is no solution feed pump or solution inlet nozzle to direct solution into the chamber 30 of the vessel 20. In the third embodiment of the invention, the growth retardant compound(s) and the solute material(s) to be precipitated are dissolved in the SCF and introduced in the chamber 30 with the SCF through a fine nozzle 140.

In the third embodiment of the invention, one or more suitable growth retardant compounds and one or more solute materials to be precipitated are packed into the extraction column 130. A thermostat controls heaters that are used to maintain the temperature of the extraction column 130 at a predetermined constant temperature. SCF from the SCF pump 40 flows through the extraction column 130 and gets saturated with the growth retardant compound(s) and the solute material(s) to be precipitated prior to entering the chamber 30 of the vessel 20. The third embodiment of the invention is different than the first embodiment, where the growth retardant compound(s) and the solute material(s) to be precipitated are introduced into the chamber 30 as part of a solution 120 through the solution inlet nozzle 90. The third embodiment of the invention is different than the second embodiment, where the solute material(s) to be precipitated are introduced into the chamber 30 as part of a solution 121 through the solution inlet nozzle 90. Instead, in the third embodiment of the invention, both the solute material(s) to be precipitated and the growth retardant compound(s) are predissolved in the SCF and are co-injected into the chamber through the SCF nozzle 140.

Particle precipitation occurs in the third embodiment of the invention due to rapid expansion of the SCF in the chamber 30 of the vessel 20. Expansion of the SCF diminishes its solvent power resulting in supersaturation and nucleation of the solute material(s) dissolved in it. Not unlike the previously discussed embodiments of the invention, the final particle size of the particles formed in the third embodiment of the invention is also determined by nucleation kinetics. The growth retardant compound(s) present during expansion of the SCF shield the nuclei of solute material(s) by surrounding their surface, thereby minimizing the opportunities for the nuclei to coalesce and form large particles. The growth retardant compound(s) prevent inter particle interaction during and after precipitation, which aids in the prevention of particle agglomeration.

During operation of the apparatus 12 shown in FIG. 3, thermostats are used to control the temperature of the extraction column 130 and the vessel 20. The SCF pump 40 supplies SCF into the extraction column 130, Which contains the growth retardant compound(s) and the solute material(s) to be precipitated into particles thereby forming a saturated SCF solution. The saturated SCF solution is then expanded across a pressure drop into the chamber 30 of the vessel 20, preferably through the SCF nozzle 140. The pressure inside the precipitation chamber is maintained well below the critical pressure of the SCF, and preferably at atmospheric pressure, in order to facilitate maximum expansion of the SCF solution. If necessary, the backpressure regulator, 70 can be used to adjust the pressure inside the chamber 30. Once the precipitation process has been completed, the flow of the saturated SCF solution into the chamber 30 is stopped and the particles can be recovered from the chamber 30.

If desired, pure SCF can be introduced into the chamber 30 by bypassing the extraction column 130 containing the growth retardant compound(s) and the solute material(s) to be precipitated using valves. The pressure and temperature of the pure SCF stream and the pressure and temperature within the chamber 30 is maintained such that only residual growth retardant compound(s) present in the chamber 30 will become dissolved in the SCF. The flow of pure SCF through the vessel is maintained for a time sufficient to completely purge the growth retardant compound present inside the chamber 30.

The following example is intended only to illustrate the invention and should not be construed as imposing limitations upon the claims. Unless specified otherwise, all materials and equipment used in the examples can be obtained from Sigma Aldrich, Inc. (St. Louis, Mo.) and/or Fisher Scientific International, Inc. (Hanover Park, Ill.).

EXAMPLE

Acetaminophen particles were precipitated using the apparatus for the laboratory-scale production of particles described in the first embodiment of the invention. Specifically, 3.0 g of acetaminophen (the solute to be precipitated) and 3.0 g of alpha D glucose penta acetate (the growth retardant compound) were dissolved in 60 g of acetone (the solvent) to form a clear solution. Supercritical carbon dioxide ("SC—$CO_2$") was used as the supercritical fluid. The flow rate of SC—$CO_2$ was set at 75 g/min and the flow rate of the solution was set at 1.5 ml/min. A 150-micron nozzle was used to introduce the solution into the SC—$CO_2$. The operating temperature was set to 40° C. and the operating pressure was set to 80 bar. As soon as the solution was introduced, mass transfer of acetone into the SC—$CO_2$ occurred, which led to supersaturation and the formation of nuclei of acetaminophen in the presence of alpha D glucose penta acetate. The alpha D glucose penta acetate acted as a growth retardant compound in that it immediately surrounded the acetaminophen nuclei, thereby preventing them from coalescing to form larger particles.

After precipitation was complete, the alpha D glucose penta acetate present in the precipitation vessel was removed using a continuous flow of pure SC—$CO_2$ at 40° C. and 80 bar. The vessel was then depressurized and the particles were collected for analysis.

Figure 4A:
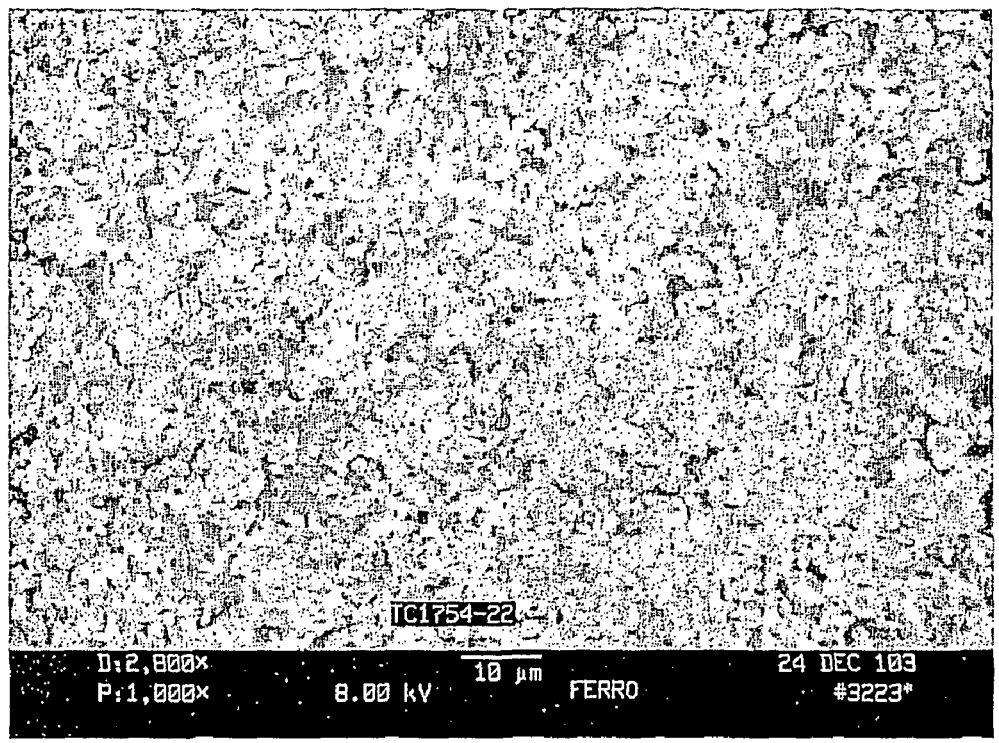
FIGS. 4A and 4B are scanning electron micrographs of particles formed in the Example below.
Figure 4B:
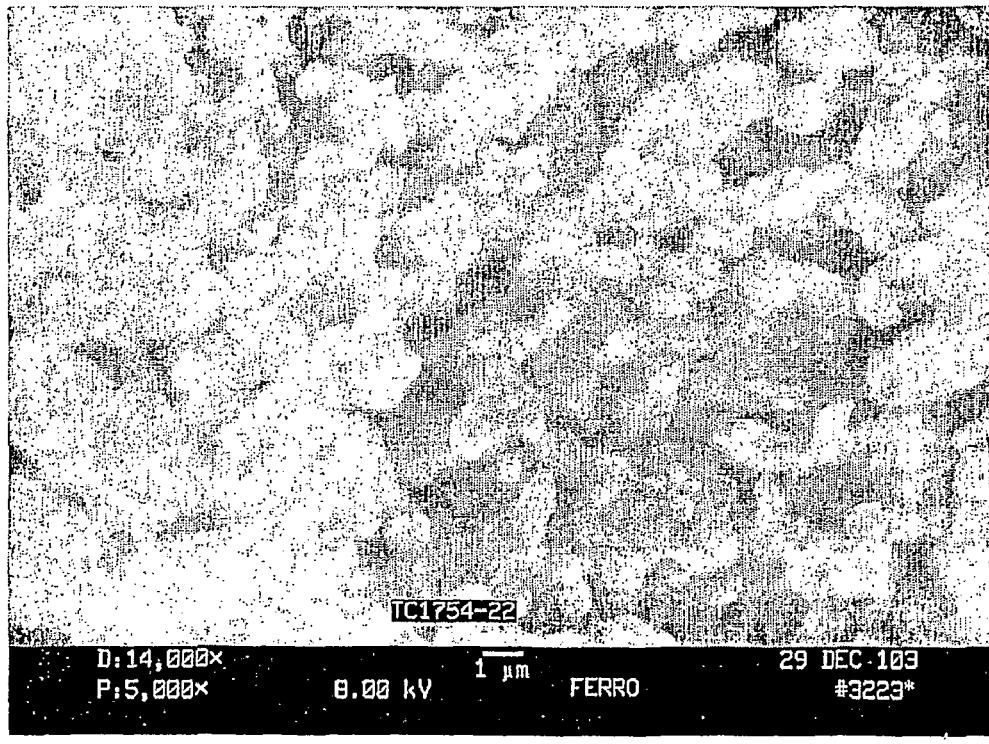

FIGS. 4A and 4B are scanning electron micrographs of the acetaminophen particles formed in the Example at two magnifications. The micrographs show that the acetaminophen appear to be substantially uniform in size (~1-2 microns) and circular in shape. Some minimal particle agglomeration or bridging is apparent.

Figure 5:
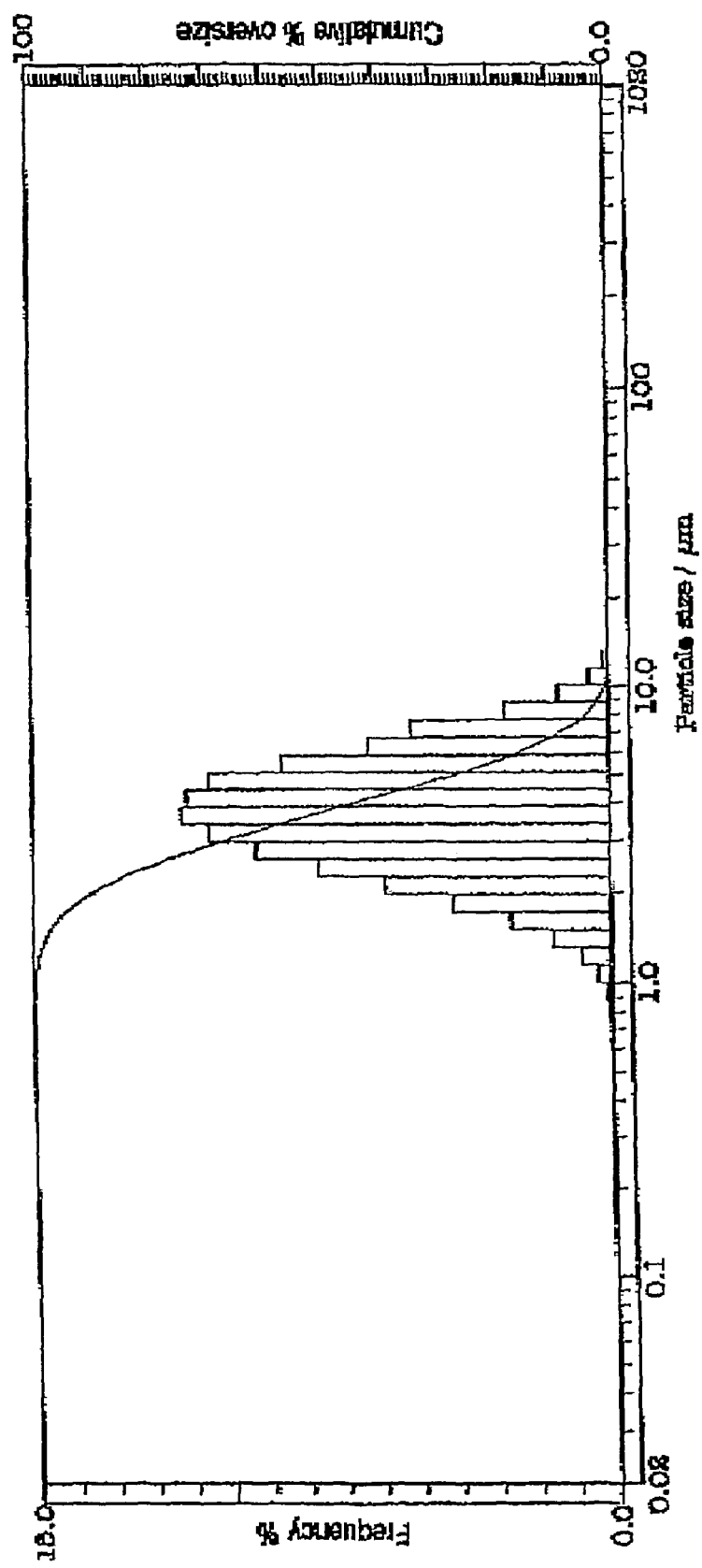
FIG. 5 is a graph showing the size distribution of particles formed in the Example below.

The mean diameter of the acetaminophen particles formed in the Example was measured using the conventional laser light scattering technique, which is known in the art. FIG. 5 is a graph showing the size distribution of particles. The mean volume diameter of the particles was 4.08 microns and the standard deviation was 1.87 microns.

The foregoing Example demonstrates that particles precipitated in the presence of a growth retardant compound tend to have a smaller particle size and a greater degree of uniformity (both in size and in morphology) than can be obtained using conventional supercritical fluid anti-solvent techniques.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of producing particles using supercritical fluid (SCF) comprising:
   providing a source of SCF;
   dissolving at least one solute material and at least one growth retardant compound in the SCF to form an SCF solution, wherein the growth retardant compound includes at least one functional group or portion that is SCF-philic and at least one functional group or portion that is SCF-phobic or solute material-philic; and
   expanding SCF solution across a pressure drop below the critical pressure of the SCF whereby the SCF decompresses and causes supersaturation and nucleation of particles comprising the solute material, said particles having a smaller size and a reduced amount of agglomeration than if no growth retardant compound was present.

2. The method according to claim 1 wherein the SCF is supercritical carbon dioxide.

3. The method according to claim 2 wherein the growth retardant compound is selected from the group consisting of sugar acetates, fluorocarbons and block copolymers.

4. The method according to claim 3 wherein the block copolymer is comprised of polymer blocks selected from the group consisting of polypropylene oxide, poly methacrylic acid (PMMA), poly acrylic acid (PAA), poly vinyl acetate (PVA) and polyethylene oxide (PEO).

5. The method according to claim 1 wherein the solute material is selected from the group consisting of medicinal agents, biologically active materials, sugars, viral materials, diagnostic aids, nutritional materials, proteins, peptides, animal extracts, plant extracts and combinations thereof.

6. The method according to claim 5 wherein the solution further comprises a second solute material selected from the group consisting of polymers, fillers, disintegrants, binders, solubilizers, excipients, and combinations thereof. In particular, the matrix materials can be, for example, polysaccharides, polyesters, polyethers, polyanhydrides, polyglycolides (PLGA), polylactic acids (PLA), polycaprolactones (PCL), polyethylene glycols (PEG), polypeptides and combinations thereof.

7. The method according to claim 6 wherein the particles have an average particle size of less than 10 micron and more than 300 nm.

* * * * *